US009447475B2

(12) United States Patent
Kitta et al.

(10) Patent No.: US 9,447,475 B2
(45) Date of Patent: *Sep. 20, 2016

(54) METHOD FOR DETECTING AND QUANTIFYING WHEAT ENDOGENOUS GENE

(71) Applicant: Nisshin Seifun Group Inc., Tokyo (JP)

(72) Inventors: Kazumi Kitta, Tsukuba (JP); Satoshi Furui, Tsukuba (JP); Junichi Mano, Tsukuba (JP); Shinjiro Imai, Saitama (JP); Keiko Tanaka, Saitama (JP); Yasuyuki Matsuoka, Atsugi (JP); Shinichiro Arami, Atsugi (JP); Megumi Sato, Atsugi (JP); Hiroyuki Haraguchi, Atsugi (JP); Youichi Kurimoto, Atsugi (JP)

(73) Assignee: NISSHIN SEIFUN GROUP INC., Tokyo (JP)

( * ) Notice: Subject to any disclaimer, the term of this patent is extended or adjusted under 35 U.S.C. 154(b) by 7 days.

This patent is subject to a terminal disclaimer.

(21) Appl. No.: 14/189,575

(22) Filed: Feb. 25, 2014

(65) Prior Publication Data

US 2014/0288289 A1   Sep. 25, 2014

Related U.S. Application Data

(62) Division of application No. 13/517,453, filed as application No. PCT/JP2010/072809 on Dec. 17, 2010, now Pat. No. 9,273,362.

(30) Foreign Application Priority Data

Dec. 21, 2009 (JP) ................. 2009-289137

(51) Int. Cl.
*C07H 21/04* (2006.01)
*C12Q 1/68* (2006.01)

(52) U.S. Cl.
CPC ............. *C12Q 1/6895* (2013.01); *C07H 21/04* (2013.01); *C12Q 2545/113* (2013.01)

(58) Field of Classification Search
None
See application file for complete search history.

(56) References Cited

U.S. PATENT DOCUMENTS

| | | |
|---|---|---|
| 8,030,463 B2 | 10/2011 | Hino et al. |
| 8,173,400 B2 | 5/2012 | Imai et al. |
| 2009/0011411 A1 | 1/2009 | Hino et al. |
| 2010/0062432 A1 | 3/2010 | Imai et al. |
| 2011/0265222 A1 | 10/2011 | Ayal et al. |
| 2012/0009584 A1 | 1/2012 | Hino et al. |
| 2012/0009585 A1 | 1/2012 | Hino et al. |
| 2012/0009586 A1 | 1/2012 | Hino et al. |
| 2012/0040862 A1 | 2/2012 | Hino et al. |
| 2012/0208992 A1 | 8/2012 | Imai et al. |
| 2012/0214161 A1 | 8/2012 | Imai et al. |
| 2012/0246748 A1 | 9/2012 | Guo et al. |
| 2013/0115614 A1 | 5/2013 | Hino et al. |

FOREIGN PATENT DOCUMENTS

| | | |
|---|---|---|
| EP | 1 482 058 A1 | 12/2004 |
| EP | 1 736 543 A1 | 12/2006 |
| EP | 2 019 136 A1 | 1/2009 |
| JP | 6-125669 A | 5/1994 |
| JP | 7-501682 A | 2/1995 |
| JP | 2003-284598 A | 10/2003 |
| JP | 2009-082125 A | 4/2009 |
| WO | WO 91/13991 A1 | 9/1991 |
| WO | WO 98/04737 A1 | 2/1998 |
| WO | WO 03/068989 A1 | 8/2003 |
| WO | WO 2005/097989 A1 | 10/2005 |
| WO | WO 2007/132760 A1 | 11/2007 |

OTHER PUBLICATIONS

Final Office Action for U.S. Appl. No. 13/517,453, dated Jul. 29, 2014 (30 pages).
U.S. Appl. No. 13/710,910, filed Dec. 11, 2012, by Akihiro Hino et al.: Final Office Action mailed Jan. 29, 2014.
GenBank Accession No. S79982, Lr1 (TLR621)=leaf rust resistance gene [Triticum aestivum=wheat, Genomic, 915 nt] (Feb. 12, 1997), retrieved from https://www.ncbi.nlm.nih.gov/nuccore/S79982.
Japanese Patent Application No. 2009-289137, filed Dec. 21, 2009, by National Agriculture & Food Research Organization et al., inventors Kitta et al.: Notice of Reasons for Rejection, mailed Feb. 28, 2014, with English translation (7 pages).
U.S. Appl. No. 13/366,062, filed Feb. 3, 2012, by Imai et al.: Final Office Action, mailed Mar. 19, 2014.
Japan Ministry of Health, Labor and Welfare, The Food Sanitation Department, "Concerning Testing Methods for Foods Modified by Recombinant DNA Technology (Partially Revised)", Notice No. 0618001, pp. 1-18 (Jun. 18, 2003).
Japan Ministry of Health, Labor and Welfare, The Food Sanitation Department, "Concerning Testing Methods for Foods Modified by Recombinant DNA Technology (Partially Revised)", Notice No. 1113001, p. 1 (Nov. 13, 2003).
Japan Ministry of Health, Labor and Welfare, The Food Sanitation Department, "Manual of Assessment and Analysis for Genetically Modified Foods", Japanese Agricultural Standard (JAS) Analytical Test Handbook, Revised Second Edition. 70 pages (Jun. 20, 2002).
"Manual of Assessment and Analysis for Genetically Modified Foods," Revised Second Edition; JAS Analytical Test Handbook, Jun. 18, 2003.

(Continued)

*Primary Examiner* — David Thomas
(74) *Attorney, Agent, or Firm* — Finnegan, Henderson, Farabow, Garrett & Dunner, L.L.P.

(57) ABSTRACT

Provided is a method of detecting or quantifying a wheat species-specific DNA in a test sample by polymerase chain reaction. The method comprises a step of amplifying a nucleic acid molecule having at partial sequence of a nucleotide sequence identified as SEQ ID NO: 1 using a nucleic acid molecule in the test sample or a nucleic acid molecule extracted from the test sample as the template and using a primer pair capable of amplifying the partial sequence and a step of detecting or quantifying the amplified nucleic acid molecule.

1 Claim, 4 Drawing Sheets

(56) References Cited

OTHER PUBLICATIONS

Ahern, "Biochemical, Reagent Kits Offer Scientists Good Return on Investment" The Scientist, 20:20,22 (Jul. 24, 1995).

Ainsworth, Charles, et al.; "Expression, Organisation and Structure of the Genes Encoding the Waxy Protein (Granule-Bound Starch Synthase) in Wheat" Plant Molecular Biology, 22:67-82 (1993).

Allmann, Michael, et al., "Polymerase chain reaction (PCR): A possible alternative to immunochemical methods assuring safety and quality of food" Z. Lebensm. Unters Forsch., 196:248-251 (1993).

Aoki et al. "Three Sucrose Transporter Genes Are Expressed in the Developing Grain of Hexaploid Wheat" Plant Molecular Biology, 50:453-462 (2002).

European Search Report in corresponding EP Application No. 05728798.9, dated Apr. 17, 2009.

European Search Report in corresponding EP Application No. 07743162.5, dated Jun. 10, 2010.

European Search Report in corresponding EP Application No. 09015931.0, dated Apr. 14, 2010.

European Search Report in corresponding EP Application No. 09015932.8, dated Apr. 12, 2010.

Feuillet et al., "Genetic and Physical Characterization of the LR1 Leaf Rust Resistance Locus in Wheat (*Triticum Aestivum* L.)," Molecular and General Genetics, 248(5):553-562 (1995).

GenBank Accession No. AF113844, Triticum aestivum granule-bound starch synthase precursor (Wx-D1) mRNA, Wx-D1b allele, complete cds (Apr. 20, 1999).

GenBank Accession No. AF408845, Triticum aestivum sucrose transporter SUT1D gene, complete cds (Mar. 19, 2002).

GenBank Accession No. AJ440705, Triticum aestivum GSS clone PSR1205 forward sequence, genomic survey sequence (Jul. 31, 2003).

GenBank Accession No. BT008973 (retrieved on-line), Jun. 2003, retrieved from http://www.ncbi.nlm.nih.gov/nuccore/BT008973.

GenBank Accession No. J02817, Wheat gibberellin responsive protein gene, complete cds (Apr. 27, 1993).

GenBank Accession No. S79982, Lr1 (TLR621)=leaf rust resistance gene [Triticum aestivum=wheat, Genomic, 915 nt] (Feb. 12, 1997).

GenBank Accession No. S79983, Lr1 (TH621)=leaf rust resistance gene [Triticum aestivum=wheat, Genomic, 892 nt] (Feb. 12, 1997).

GenBank Accession No. X52472; Raines, C.A. et al.; "T. aestivum mRNA for a proline-rich protein;" retrieved on Sep. 12, 1993 from www.ncbi.nlm.nih.gov/entrez/viewer.fcgi?db=nucleotideval=21841.

Hübner, Philipp, et al., "Validation of PCR Methods for Quantitation of Genetically Modified Plants in Food" Journal of AOAC International, 84(6):1855-1864 (2001).

Iida, Mayu, et al., "Development of Taxon-Specific Sequences of Common Wheat for the Detection of Genetically Modified Wheat" Journal of Agricultural and Food Chemistry, 53:6294-6300 (2005).

International Search Report and Written Opinion for International Patent Application No. PCT/JP2005/006784, dated Jul. 19, 2005, English translations.

International Search Report and Written Opinion for International Application No. PCT/JP2007/059727, dated Jan. 15, 2009.

International Preliminary Report on Patentability for International Application No. PCT/JP2010/072809, issued Jul. 10, 2012.

International Search Report and Written Opinion from the Japanese Patent Office for International Application No. PCT/JP2010/072809, mailed Jan. 25, 2011.

Köppel et al., "Sensitive Nachweismethode für die gentechnisch veränderte Sojabohne <<Roundup Ready™>> (Sensitive Method for the Detection of the Genetically Engineered Soy Bean <<Roundup Ready™>>)" Mitt. Gebiete Lebensm, Hyg., 88:164-175 (1997). (English summary on p. 173-174.).

Ling et al., "High-Resolution Mapping of the Leaf Rust Disease Resistance Gene Lr1 in Wheat and Characterization of BAC Clones From the Lr1 Locus" Theoretical and Applied Genetics, 106(5):875-882 (2003).

Lowe et al., "A computer program for selection of oligonucleotide primers for polymerase chain reactions" Nucleic Acids Research, 18(7):1757-1761 (1990).

McNeil et al., "Amplification of DNA sequences in wheat and its relatives: the Dgas44 and R350 families of repetitive sequences" Genome, 37(2):320-327 (1994).

Murai et al., "Isolation and Characterization of the Three Waxy Genes Encoding the Granule-Bound Starch Synthase in Hexaploid Wheat" Gene, 234:71-79 (1999).

Nakamura et al., "Rapid classification of partial waxy wheats using PCR-based markers" Genome, 45(6):1150-1156 (2002).

Raines et al., "A novel proline-rich protein from wheat" Plant Mol. Biol., 16(4):663-670 (1991).

Ronning et al., "Novel Reference Gene, PKABA1, Used in a Duplex Real-Time Polymerase Chain Reaction for Detection and Quantitation of Wheat- and Barley-Derived DNA", Journal of Agricultural and Food Chemistry, 54:682-687 (2006).

Studer, Edgar, et al., "Quantitative Competitive PCR for the Detection of Genetically Modified Soybean and Maize" Z. Lebensm. Unters Forsch. A, 207:207-213 (1998).

Terzi, Valeria, et al., "Development of Analytical Systems based on Real-Time PCR for Triticum Species-Specific Detection and Quantitation of Bread Wheat Contamination in Semolina and Pasta" Journal of Cereal Science, 38:87-94 (2003).

U.S. Appl. No. 13/218,385, filed Aug. 25, 2011, by Hino et al.: Non-Final Office Action, dated Sep. 16, 2013.

U.S. Appl. No. 13/366,062, filed Feb. 3, 2012, by Imai et al.: Advisory Action, dated Jun. 12, 2013.

U.S. Appl. No. 13/366,062, filed Feb. 3, 2012, by Imai et al.: Non-Final Office Action, mailed Sep. 23, 2013.

U.S. Appl. No. 13/366,190, filed Feb. 3, 2013, by Imai et al.: Advisory Action, mailed Aug. 12, 2013.

U.S. Appl. No. 13/366,190, filed Feb. 3, 2013, by Imai et al.: Advisory Action, mailed Sep. 19, 2013.

U.S. Appl. No. 13/710,910, filed Dec. 11, 2012, by Hino et al.: Non-final Office Action, dated Jul. 5, 2013.

U.S. Appl. No. 13/517,453, filed Jun. 20, 2012, by Kitta et al.: Non-final Office Action, dated Jan. 13, 2014.

Waiblinger et al., "A Screening Method for the Identification of 'Genetically Modified' Food of Plant Origin" Foods Produced by Means of Genetic Engineering, 2nd Status Report: BgVV, BgVV-Heft, pp. 118-122, (1997).

Yamakawa, Hirohito, et al., "Specific Detection of Wheat Residues in Processed Foods by Polymerase Chain Reaction" Bioscience, Biotechnology, and Biochemistry, 71(10):2561-2564 (2007).

Yan et al., "Sequences of the Waxy Loci of Wheat: Utility in Analysis of Waxy Proteins and Developing Molecular Markers," Biochemical Genetics, 38(11/12): 391-411 (2000).

Yang et al., "Genomics, Molecular Genetic & Biotechnology. A Rapid and Direct Approach to Identify Promoters That Confer High Levels of Gene Expression in Monocots" Crop Science, 43:1805-1813 (2003).

Decision of Rejection dated Oct. 31, 2014, issued for Japanese Patent Application No. 2009-289137, with English Translation (6 pages total).

Office Action issued in European Patent Application No. 10 839 324.0 mailed on Dec. 20, 2013.

US 9,447,475 B2

METHOD FOR DETECTING AND QUANTIFYING WHEAT ENDOGENOUS GENE

CROSS REFERENCE TO RELATED APPLICATIONS

This application is a divisional of application Ser. No. 13/517,453, whose 35 U.S.C. §371(c) date is Jun. 20, 2012, which is a national phase application of International Application No. PCT/JP2010/072809, filed Dec. 17, 2010, and claims the priority of Japanese Patent Application No. 2009-289137, filed Dec. 21, 2009, the contents of all of which are incorporated herein by reference.

TECHNICAL FIELD

The present invention relates to a method of detecting and quantifying an endogenous gene of wheat (hereinafter, referred to as "species-specific gene") in a test sample. In particular, the invention relates to a method of detecting and quantifying a wheat endogenous DNA (hereinafter, referred to as "species-specific DNA"), which is used for determining the contamination rate of genetically modified wheat contained in food materials or processed foods.

BACKGROUND ART

Japan has already approved importing and selling 50 or more varieties of genetically modified crops (hereinafter, referred to as "GMOs") such as corn, soybeans, and potato that have passed safety assessment. In connection with this, GMO-containing foods must be labeled in accordance with "the Labeling Standards for Genetically Modified Foods established by the Ministry of Agriculture, Forestry and Fisheries based on Article 7, paragraph 1 of the Quality Labeling Standard for Processed Foods and Article 7, paragraph 1 of the Quality Labeling Standard for Fresh Food" (Notification No. 517 of the Ministry of Agriculture, Forestry and Fisheries, Mar. 31, 2000) and "the Enforcement of Ministerial Ordinance amending in part the Ministerial Ordinance on Food Sanitation Law Enforcement Regulations and Compositional Standards, etc. for Milk and Milk Products" (Notice No. 79 of the Food Sanitation Department, Ministry of Health, Labor and Welfare, Mar. 15, 2001).

In other countries, however, GMOs may be cultivated in some cases together with non-GMOs once the safety evaluation thereof has been completed, or contamination may occur during the process of distribution after harvest. Moreover, many food processors and the like often contract the manufacture of processed foods to manufacturing companies, and even if they stipulate that non-GMOs should, be used, if GMOs are used in the plants of the manufacturing companies, small quantities of such GMOs may contaminate processed foods. Consequently, in order to fulfill their labeling obligations, food processors and the like must assess and analyze the final processed food products to confirm that they are not contaminated by GMOs.

Known methods of detecting GMOs in test samples of processed foods, raw materials thereof, etc. include a method of detecting a recombinant DNA by polymerase chain reaction (hereinafter, referred to as "PCR") and a method of detecting a recombinant protein by an enzyme-linked immunosorbent assay (hereinafter, referred to as "ELISA"). In the case of processed foods, many proteins are denatured due to heating or pressurizing and cannot be, thereby, correctly detected by ELISA in many cases. Consequently, detection by PCR is commonly performed.

Known methods for assessment and analysis of GMOs include the method described in "the JAS Analytical Handbook, Manual of Assessment and Analysis for Genetically Modified Foods, Revised Second Edition" and the method described in "Concerning Testing Methods for Foods Modified by Recombinant DNA Technology (Partially Revised)" (Notice No. 0618002 of the Food Sanitation Department, Ministry of Health, Labor and Welfare, Jun. 18, 2003). These describe that in the testing and analysis of GMOs, in order to confirm whether DNA extracted from a test sample can be amplified by PCR, it is necessary to confirm whether a PCR product having an expected length is obtained by PCR using a primer pair recognizing a species-specific DMA of each agricultural product. In quantification of a GMO contained in a test sample, the contamination rate of a recombinant is relatively determined based on the abundance ratio of a recombinant DNA to a species-specific DNA that is always present in the crop.

For example, in the case of corn, primer pairs that specifically recognize respectively the five lines of approved GMO strains have been developed, and also a primer pair that recognizes the SSIIB gene region has been developed as a corn species-specific DNA.

Because this primer pair that recognizes the species-specific DNA provides a standard for the amount of the species-specific DNA in recombinant DNA detection and quantification, the region of the species-specific DNA to be amplified should be present in a single copy on the genome. In "Concerning Testing Methods for Foods Modified by Recombinant DNA Technology (Partially Revised)" (Notice No. 1113001 of the Food Sanitation Department, Ministry of Health, Labor and Welfare, Nov. 13, 2003), quantitative PCR is performed using a standard substance that is an amplification product amplified by a specific primer pair targeting a corn or soybean species-specific DNA and a recombinant DNA and linked to a plasmid. The ratio of the number of copies of the recombinant DNA to the number of copies of the species-specific DNA can be accurately determined by performing the quantitative PCR using this standard substance and also performing the quantitative PCR of a test sample for a predetermined time.

When there are multiple lines of GMO strains, as in corn, use of a standard substance where a DNA specific to any line and a species-specific DNA are linked to a single circular DNA usefully allows use of a common standard substance in measurement of the contamination rate of any line.

It is generally difficult to obtain a gene specific to any line, but once a replicable DNA containing it has been prepared, a line-specific DNA can be also stably obtained by replicating this DNA itself.

CITATION LIST

Non Patent Literature

[Non Patent Literature 1]
"The Labeling Standards tor Genetically Modified Foods established by the Ministry of Agriculture, Forestry and Fisheries based on Article 7, paragraph 1 of the Quality Labeling Standard for Processed Foods and Article 7, paragraph 1 of the Quality Labeling Standard for Fresh Food" (Notification No. 517 of the Ministry of Agriculture, Forestry and Fisheries, Mar. 31, 2000)

[Non Patent Literature 2]

"The Enforcement of Ministerial Ordinance amending in part the Ministerial Ordinance on Food Sanitation Law Enforcement Regulations and Compositional Standards, etc. for Milk and Milk Products" (Notice No. 79 of the Food Sanitation Department, Ministry of Health, Labor and Welfare, Mar. 15, 2001).

[Non Patent Literature 3]

The JAS Analytical Handbook, Manual of Assessment and Analysis for Genetically Modified Foods, Revised Second Edition

[Non Patent Literature 4]

"Concerning Testing Methods for Foods Modified by Recombinant DNA Technology (Partially Revised)" (Notice No. 0618002 of the Food Sanitation Department, Ministry of Health, Labor and Welfare, Jun. 18, 2003)

[Non Patent Literature 5]

Kopell, E. et al.; Mitteilungen aus dem Gebiete der Lebensmitteluntersuchung and Hygiene, 86, 164, published by Neukomm & Zimmermann (Berne)

SUMMARY OF INVENTION

Technical Problem

While genetically modified products of bread wheat do not have yet passed safety assessment, such products are expected to appear on the market in the near future. Consequently, there is a demand for developing a method for detecting and quantifying a wheat species-specific DNA and PCR primer pairs for use in such a method, in preparation for distribution of GMO wheat.

Wheat exists in various forms of gene compared to other grain. This is caused by the presence of genotypes of hexaploid, tetraploid, and diploid in wheat strains. The genotype of common bread wheat is hexaploid. Their respective genes resemble each other, but have partial differences due to, for example, translocation. Because of these reasons, wheat has variations in the genotypes depending on the strains, and a species-specific gene of wheat that satisfies the following requirements is not found, yet:

A) being ubiquitous in wheat stains;
B) not varying in the abundance (detection amount) regardless of wheat strains;
C) not affected in its detection by other grains; and
D) being quantitatively amplified by PCR.

Wheat has a high homology with other cereals such as barley, rye, and oats in terms of the genome structure and the nucleotide sequences of encoding genes. These cereals have nigh homologies with bread wheat and have high possibilities of false detection as bread wheat. There is therefore a demand for a method that does not cross-react with other crops in order to specifically detect only a species-specific DNA of bread wheat without falsely detecting DNAs derived from other cereals and crops.

In addition, if a species-specific DNA region that will be amplified by PCR is present in multiple copies, accurate quantification of wheat in a test sample is difficult. Accordingly, in order to accurately quantify the contamination rate of GMO wheat in a test sample, it is desirable that the species-specific DNA region that will be amplified be present on the genome with a constant rate.

Moreover, in the case of determining the contamination rate of a GMO by quantitative PCR, for wheat, use of a standard substance where a region that can be amplified by a specific primer pair targeting a species-specific gene DNA and a recombinant DNA is linked on a circular DNA is also useful.

Accordingly, it is an object of the present invention to provide a method suitable for detection and quantification of a species-specific DNA using PCR primers that specify and amplify a wheat DNA (genome) partial region being ubiquitous in wheat stains, not varying in the abundance (detection amount), and do not cross-react with other plants.

It is another object of the present invention to provide a standard substance where a region that can be amplified by a specific primer pair targeting a wheat species-specific DNA and a recombinant DNA is linked on a circular DNA.

Solution to Problem

The present inventors have intensively studied in order to solve the above-mentioned problems and, as a result, have found that a partial region of the proline rich protein (PRP) gene described in Raines C A, Lloyd J C, Chao SM, John UP, and Murphy GJ, A novel proline-rich protein from wheat, Plant Mol. Biol., 1991, Apr. 16(4): 663-70 is ubiquitous in the wheat genomic DNA of wheat regardless of wheat strains. Furthermore, the present inventors have found that the partial region of the PRP gene can be amplified by PCR without cross-reactivity with other plants and can be specifically detected or quantified as a wheat species-specific DNA sequence, and have accomplished the present invention.

That is, the gist of a first aspect of the present invention is a method of detecting or quantifying a wheat species-specific DNA in a test sample by PCR, the method comprising a step of amplifying a nucleic acid molecule having a partial sequence of a nucleotide sequence identified as SEQ ID NO: 1 using a nucleic acid molecule in the test sample or a nucleic acid molecule extracted from the test sample as the template and using a primer pair capable of amplifying the partial sequence and a step of detecting or quantifying the amplified nucleic acid molecule.

In the first aspect of the present invention, the primer pair may be selected from a primer pair consisting of a nucleic acid molecule comprising the nucleotide sequence identified as SEQ ID NO: 2 and a nucleic acid molecule comprising the nucleotide sequence identified as SEQ ID NO: 3; a primer pair consisting of a nucleic acid molecule comprising the nucleotide sequence identified as SEQ ID NO: 4 and a nucleic acid molecule comprising the nucleotide sequence identified as SEQ ID NO: 3; and a primer pair consisting of a nucleic acid molecule comprising the nucleotide sequence identified as SEQ ID NO: 2 and a nucleic acid molecule comprising the nucleotide sequence identified as SEQ ID NO: 5. Alternatively, the primer pair may be selected from a primer pair consisting of a nucleic acid molecule comprising the nucleotide sequence identified as SEQ ID NO: 4 and a nucleic acid molecule comprising the nucleotide sequence identified as SEQ ID NO: 5; a primer pair consisting of a nucleic acid molecule comprising the nucleotide sequence identified as SEQ ID NO: 2 and a nucleic acid molecule comprising the nucleotide sequence identified as SEQ ID NO: 6; and a primer pair consisting of a nucleic acid molecule comprising the nucleotide sequence identified as SEQ ID NO: 2 and a nucleic acid molecule comprising the nucleotide sequence identified as SEQ ID NO: 7. Furthermore, the primer pair may be selected from a primer pair consisting of a nucleic acid molecule comprising the nucleotide sequence identified as SEQ ID NO: 4 and a nucleic acid molecule comprising the nucleotide sequence identified as SEQ ID NO: 7; and a primer pair consisting of a nucleic acid molecule comprising the nucleotide sequence identified as SEQ ID NO: 4 and a nucleic acid molecule comprising the nucleotide sequence identified as SEQ ID NO: 6. In addition, the primer pair may be any of primer pairs each comprising continuous nucleotide sequences of at least 80% of the nucleotide sequences possessed by the respective nucleic acid molecules of the primer pairs described above.

In the first aspect of the present invention, the primers of the primer pair may be nucleic acid molecules each having a length of 15 to 40 nucleotides.

The gist of a second aspect of the present invention is a kit for detecting or quantifying a wheat species-specific DNA sequence in a test sample by PCR, the kit comprising the above-mentioned primer pair.

The gist of a third aspect of the present invention is a replicable DNA comprising a species-specific DNA common to both genetically modified wheat and non-genetically modified wheat and at least one genetically modified wheat-specific DNA including a sequence specific to any line of the genetically modified wheat. The replicable DNA refers to a DNA having a replication origin specific to a host.

The gist of a fourth aspect of the present invention is a replicable circular DNA comprising a DNA consisting of a nucleotide sequence having a homology of at least 80% with the nucleotide sequence identified as SEQ ID NO: 1. The replicable circular DNA may further contain at least one DNA including a sequence specific to any line of genetically modified wheat.

The gist of a fifth aspect of the present invention is a replicable DNA comprising a region that can be amplified by PCR using the above-described primer pair. The replicable DNA may further contain at least one DNA consisting of a sequence specific to any line of genetically modified wheat.

The gist of a sixth aspect of the present invention is a method of determining a contamination rate of genetically modified wheat in a test sample, the method comprising a first step of preparing calibration curves for a partial region of a wheat species-specific DNA sequence and a partial region of at least one DNA sequence specific to any line of genetically modified wheat by preparing two or more dilution series of a solution containing the replicable DNA according to any one of the third to fifth aspects of the present invention and subjecting each dilution series to quantitative PCR for amplifying the partial regions; and a second step of determining the number of molecules of the partial region of a wheat species-specific DNA sequence and the number of molecules of the partial region of at least one DNA sequence specific to any line of genetically modified wheat present in a test sample by amplifying the partial regions contained in the sample by quantitative PCR under the same conditions as those in the first step and using the calibration curves determined in the first step.

In the aspect according to the sixth aspect of the invention, the method may further comprise a step of determining a contamination rate of genetically modified wheat in a test sample by calculating by an expression, 100×A/B, wherein A represents a ratio obtained by dividing the number of molecules of the partial region of a DNA sequence specific to genetically modified wheat by the number of molecules of the partial region of a wheat species-specific DNA sequence determined in the second step; and B represents a ratio obtained by dividing the number of molecules of a partial region of a DNA sequence specific to any line of genetically modified wheat determined by quantitative PCR using a standard seed of genetically modified wheat by the number of molecules of the partial region of a wheat species-specific DNA sequence.

In the method according to the sixth embodiment of the present invention, the wheat species-specific DNA sequence may be amplified using at least one primer pair selected from the primer pairs mentioned above.

The PCR primer pair used in the method according to an aspect of the present invention species-specifically detects wheat and does not cross-react with crops other than wheat, such as rice, barley, rye, oats, rapeseed, corn, foxtail millet, millet, and buckwheat. Accordingly, the method according to an aspect of the present invention can provide accurate information of the presence of wheat and the amount thereof in a test sample such as a food material or a processed food.

In a testing method, if a PCR primer pair cross-reacts with a crop other than wheat, not only a false positive result may be caused in wheat detection, but also accurate quantification of a wheat species-specific DNA in a test sample may be difficult. In addition, the region of a species-specific DNA to be amplified in a detection method must be ubiquitous among wheat strains with a constant abundance. If the abundances of the species-specific DNA region among wheat strains are not the same, the wheat species-specific DNA cannot be accurately quantified. Consequently, such a method and such a primer pair cannot accurately determine the contamination rate of GMO wheat.

The present invention provides a method of specifically detecting or quantifying a wheat species-specific DNA in a test sample such as a food material or a processed food without cross-react with other crops and provides a PCR primer pair used in the method. The method according to the present invention detects or quantifies by PCR a partial region that is specific to a wheat species-specific DNA sequence, has a low homology with grains other than wheat, and is present in a single copy on the genome. Furthermore, the use of a standard substance provided by the method according to the present invention for detecting GMO wheat enables determination of the contamination rates of respective GMO wheat lines in a test sample by quantitative PCR with high accuracy.

DESCRIPTION OF EMBODIMENT

Figure 1:
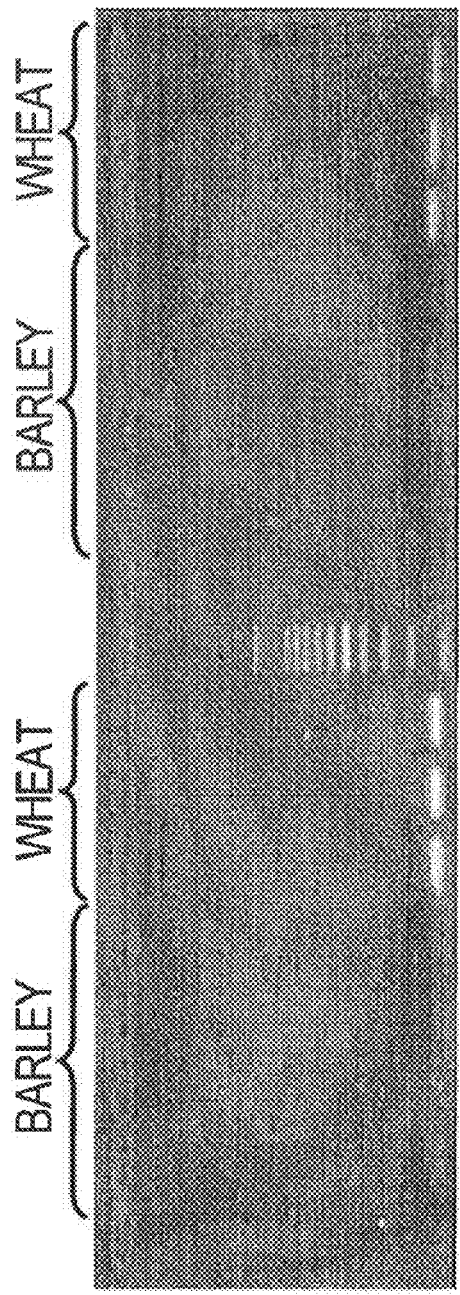
FIG. 1 is a photograph showing the results in Example 2 of the present invention.

The terms used in the specification are defined below, and an embodiment of the present invention will be described in detail.

Throughout the specification, the term "wheat" means bread wheat unless otherwise specified.

The method according to the embodiment of the present invention detects a specific part of a PRP gene region on the wheat genome as wheat species-specific DNA sequence.

Among the Waxy genes described in Raines C A, Lloyd JC, Chao SM, John UP, and Murphy GJ, A novel proline-rich protein from, wheat, Plant Mol. Biol., 1991, Apr. 16(4): 663-70, the Wx012 region described in International Publication No. WO2005/097989 cannot be detected in durum wheat. Accordingly, the Wx012 region is thought to be on the wheat D genome. In comparison of the detection amount of the Waxy gene and the detection amount of the PRP gene in each wheat strain, the amount of the Wx012 region and the amount of the gene region identified as SEQ ID NO: 1 in the PRP gene are approximately the same, while the ratio of the amount of the Wx012 region to that of the region of the PRP gene other than the gene region identified as SEQ ID NO: 1 varies from 1:1 to 1:3 depending the strains. This suggests that the PRP gene does not contain a PRP-3 region, but contains a region similar to a PRP-1 region. The detection amount of the gene region identified as SEQ ID NO: 1 is approximately the same as that of Wx012, and the gene region identified as SEQ ID NO: 1 is also detected in durum wheat. This suggests that the gene region is located on genome A or B of the wheat genome. In the case of estimating the contamination rate of a genetically modified strain where a wheat gene is modified, it is necessary that the species-specific gene is ubiquitous among wheat strains at a constant abundance. At present, in addition to bread wheat, for example, durum wheat and waxy wheat are distributed on the market. Accordingly, the species-specific gene to be detected is preferably a gene commonly present in these wheat strains at a constant abundance regardless the stains. That is, since the bread wheat strains distributed on the market each inevitably have genome A or B, a gene located on genome A or B is preferred sis the species-specific gene.

There are pseudo genes that are highly similar to the PRP gene. Accordingly, short partial sequences randomly selected from full length of the PRP gene of a wheat genome in a processed food may cause amplification of regions from several genes other than the PRP gene. That is, there may be cases in which the amounts of amplified DNAs per unit wheat are not constant in some wheat stains. Accordingly, the present inventors have intensively studied and, as a result, have found that the gene region identified as SEQ ID NO: 1 in the PRP gene region does not cross-react with the pseudogenes. The method according to the embodiment of the present invention defects and quantifies a wheat species-specific DNA by amplifying a DNA containing the gene region identified as SEQ ID NO: 1 by PCR.

The gene region identified as SEQ ID NO: 1 has a length of about 330 bp and is thus significantly short compared to the genome full length. Consequently, it is possible to detect and quantify the gene region identified as SEQ ID NO: 1 as a wheat species-specific DNA even if the sample has a possibility in which DNAs are fragmented as in processed foods.

Throughout the specification, any primer pair that can amplify a DNA containing the gene region identified as SEQ ID NO: 1 can be used in PCR. The primer pair is designed based on the nucleotide sequence of a region to be amplified in accordance with a basic rule upon the primer preparation. On this occasion, each primer preferably has a similar melting temperature (Tm) revel and has a length of 15 to 40 bp, preferably 15 to 30 bp. A PCR primer pair cross-reactive with a crop other than wheat may cause false positive results in wheat detection and also may make accurate quantification of a wheat species-specific DNA sequence in a test sample difficult. On the other hand, the primer pair according to the embodiment does not cross-react with crops other than wheat and can accurately quantify a wheat species-specific DNA.

If the abundance of a species-specific DNA region to be quantified varies depending on the wheat strains, the contamination rate of genetically modified strains cannot be accurately quantified. On the other hand, the species-specific DNA region to be amplified with the primer pair according to the embodiment of the present invention is ubiquitous among wheat strains at a constant abundance.

The method according to the embodiment of the present invention provides accurate information of the presence of wheat and the amount thereof in a test sample such as a food material or a processed food. Consequently, the PCR primer pair used in the method according to the embodiment of the present invention is required to specifically detect wheat and dose not cross-react with crops other than wheat, such as rice, barley, rye, oats, rapeseed, corn, foxtail millet, millet, and buckwheat.

Examples of the primer pair that can be used without cross-reaction with crops other than wheat include (i) a primer pair consisting of a nucleic acid molecule comprising the nucleotide sequence identified as SEQ ID NO: 2 and a nucleic acid molecule comprising the nucleotide sequence identified as SEQ ID NO: 3, (ii) a primer pair consisting of a nucleic acid molecule comprising the nucleotide sequence identified as SEQ ID NO: 4 and a nucleic acid molecule comprising the nucleotide sequence identified as SEQ ID NO: 3, (iii) a primer pair consisting of a nucleic acid molecule comprising the nucleotide sequence identified as SEQ ID NO: 2 and a nucleic acid molecule comprising the nucleotide sequence identified as SEQ ID NO: 5, (iv) a primer pair consisting of a nucleic acid molecule comprising the nucleotide sequence identified as SEQ ID NO: 4 and a nucleic acid molecule comprising the nucleotide sequence identified as SEQ ID NO: 5, and primer pairs each comprising continuous nucleotide sequences of at tea at 80% of the nucleotide sequences possessed by the respective nucleic acid molecules in the primer pairs (i) to (iv) described above. These primer pairs do not cross-react with other crops and can specifically amplify the wheat species-specific DNA region.

The test sample used in the embodiment of the present invention is a food material or a processed food that contains wheat or has a possibility of containing wheat, and examples thereof include food ingredients such as raw seeds and dried seeds of wheat, wheat flour, and mix; processing intermediate materials thereof; and processed foods such sis bread and noodles. The food materials and the processed foods as test samples are not limited to foods for human and may be foods or feed such as pet foods. Crops other than wheat include food materials and all crops that are used as food materials, and examples thereof are crops such as rice, barley, rye, oats, rapeseed, corn, foxtail millet, millet, and buckwheat mentioned above.

The test sample may be subjected directly or after pulverization to nucleic acid molecule extraction or may be subjected to nucleic acid molecule extraction after washing, drying, and then pulverization. The nucleic acid molecule extracted from a test sample and used for analysis is usually a DNA. The DNA may be extracted by any known method. At present, many DNA extraction kits are commercially available and can be used for extraction of the DNA. For example, DNA may be extracted from a test sample using a DNeasy Plant Maxi kit (manufactured by QIAGEN Inc.) in accordance with the method described in Won Patent Literature 5. The concentration of the extracted DNA is determined by, for example, measurement of absorbance, and the DNA diluted to an appropriate concentration for PCR is preferably used.

In the method according to the embodiment of the present invention, the PCR can be performed in accordance with a usual method in consideration of primers and DNA polymerases to be used. On this occasion, reagents such as a PCR buffer solution, dNTP, and $MgCl_2$ may be prepared, or a commercially available kit may be used. In the PCR, one or more of the above-mentioned primer pairs may be used. The PCR conditions can be, for example, 40 cycles of a cycle of 30 seconds at 95° C., 30 seconds at 63° C., and 30 seconds at 72° C., followed by 7 minutes at 72° C. for the final reaction, but the conditions may be appropriately changed in consideration of the Tm of the primers used, the length of the region to be amplified, the concentration of the template DNA, etc.

The amplified nucleic acid molecule (PCR product) can be detected using any method capable of identifying a specific DNA fragment. The identification can be performed by, for example, agarose gel electrophoresis, acrylamide gel electrophoresis, capillary electrophoresis, hybridization, or an immunological method. In general, a PCR product is identified based on its electrophoresis pattern, and may be detected by electrophoresis, for example, 0.8% agarose gel containing ethidium bromide and confirmation of the band.

The embodiment of the present invention includes the primer pairs used in the above-described detection and quantitation method and a kit containing these primer pairs. The primers can be produced in accordance with a usual method. The kit may include the primer pairs and other reagents. The kit may contain, for example, dNTP, $MgCl_2$, a polymerase such as a Taq DNA polymerase, a buffer solution (such as Tris-HCl), glycerol, DMSO, positive control DNA, negative control DNA, and distilled water. These reagents contained in the kit may be packaged individually or may be mixed with one another and then packaged. The concentration of each reagent in the kit is not particularly limited within the range that allows the PCR according to the embodiment of the present invention. The kit may also include desirable PCR conditions and other information.

The embodiment of the present invention further provides a standard substance useful for measuring the contamination rate of GMO wheat by quantitative PCR. This standard substance is a single circular DNA on which a wheat species-specific DNA ubiquitous among both non-GMO and GMO wheat strains are linked. The standard substance may further contain one or more GMO wheat-specific DNAs linked on the circular DNA.

In the standard substance according to the embodiment of the present invention, the wheat species-specific DNA on the circular DNA may be, for example, a DNA including a nucleotide sequence having a homology of at least 80% with the nucleotide sequence identified as SEQ ID NO: 1.

The replicable DNA used as the standard substance may be any DNA in which the wheat species-specific DNA is inserted or any DNA in which the wheat species-specific DNA and a GMO wheat line-specific DNA are inserted. The standard substance can be produced using, for example, a pBR vector (e.g., pBR322 or pBR328), a pUC vector (e.g., pUC19 or pUC18), a λ-phage vector (e.g., λgt10 or λgt11), or a commercially available vector thereof to which any modification has been applied.

In some cases, the same exogenous DNA sequence as that inserted in GMO wheat is inserted in crops other than wheat to prepare GMO crops. If only the exogenous DNA sequence is detected, it may be therefore unclear whether the exogenous DNA is derived from GMO wheat or from a GMO crop other than wheat. Accordingly, in the case of detecting GMO wheat, it is preferred to amplify a region comprising species-specific sequences present upstream and downstream of the exogenous DNA sequence, compared to detection through amplification of only the exogenous DNA sequence inserted by genetic modification. Consequently, the primer for detecting a GMO line-specific sequence is preferably a primer that can amplify a region comprising an exogenous DNA sequence inserted into each line of GMO wheat and the species-specific sequences upstream and downstream thereof. Such a primer is prepared in accordance with the method described in Non Patent Literature 5, which reports on the case of soybean, or a me tried based thereon. The sequence specific to each line of GMO wheat to be inserted into the standard substance may be selected from DNA sequences that can be amplified by such a primer.

After determination of the wheat species-specific DNA and the GMO wheat-specific DNA to be inserted into the standard substance, PCR is performed using a normal wheat genome and a GMO wheat genome as the templates to clone the wheat species-specific DNA fragment and the GMO wheat-specific DNA fragment. The cloned species-specific DNA and GMO wheat-specific DNA fragments and the cloning site of the above-mentioned circular DNA are cleaved with the same restriction enzyme, and the cloned species-specific DNA and GMO wheat-specific DNA fragments are linked to the cleaved site of the circular DNA. Thus, a standard substance is produced. The restriction enzyme may be any known one appropriately selected, and, for example, EcoRI, SpeI, EcoRV, SmaI, SacI, NotI, HindIII, or XhoI can be used.

Two or more dilution series of a solution containing the resulting standard substance are prepared and are each subjected to quantitative PCR to prepare calibration curves for the partial regions of the wheat species-specific DNA sequence and the GMO-specific DNA sequence. The standard substance according to the embodiment of the present invention can also be used as a positive control for the wheat species-specific DNA sequence and the GMO-specific DNA sequence in qualitative PCR.

The embodiment of the present invention encompasses a method of determining the contamination rate of GMO wheat in a test sample by PCR using the standard substance. The method includes a first step of determining calibration curves for specific sequences by using the standard substance and a second step of determining the number of molecules of a partial region of a wheat species-specific DNA sequence and the number of molecules of a partial region of a GMO wheat-specific DNA sequence present in a rest sample by amplifying the partial regions of the wheat species-specific DNA sequence and the GMO wheat-specific DNA sequence contained in the sample by PCR, under the same conditions as those in the first step for a predetermined time, and using the calibration curves prepared in the first step.

In determination of the contamination rate of GMO wheat in the test sample, a ratio A, which is obtained by dividing the number of molecules of the partial region of a GMO wheat-specific DNA sequence contained in the test sample by the number of molecules of the partial region of a wheat species-specific DNA sequence determined in the second step, is calculated. Separately, a ratio B, which is obtained by dividing the number of molecules of a partial region of a DNA sequence specific to each line of GMO wheat determined by quantitative PCR using a standard seed of genetically modified wheat by the number of molecules of the partial region of a wheat species-specific DNA sequence, is calculated. The contamination rate of the genetically modified wheat in the test sample can be calculated by an expression: 100×A/B. The ratio B is referred to as "internal standard ratio" in Non Patent Literature 3 and is the ratio of a recombinant gene to a species-specific gene in a DNA extracted from the seed of each pure GMO line. The internal standard ratio is constant in seeds of each recombinant line.

The PCR steps in the method of determining the GMO wheat contamination rate according to the embodiment of the present invention may be performed separately or simultaneously. The PCR steps are preferably performed under conditions that allow amplification of a nucleic acid molecule to occur at a rate approximately the same as that in the PCR for preparing the calibration curve. Examples of such conditions include the same temperatures and cycles as in the PCR for preparing the calibration curve. The GMO wheat contamination rate may be calculated from the results obtained by separately measuring the amount of the species-specific DNA and the amount of the recombinant DNA. Alternatively, the GMO wheat contamination rate may be calculated from the results obtained by simultaneously amplifying the species-specific DNA and the recombinant DNA with a real time PCR apparatus in accordance with the method described in Non Patent Literature 3. In the embodiment or the present invention, the term "recombinant DNA" refers to an arbitrary exogenous DNA artificially introduced into wheat and refers to a DNA of, for example, a region encoding an exogenous gene, an untranscripted or untranslated region, a linker region, or a vector site.

EXAMPLES

Samples, reagents, apparatuses, and conditions used in the following examples are as follows.

(1) Samples

As the wheat (*Triticum aestivum*), dried seeds of four domestic wheat strains (A to D) and 19 foreign wheat strains (E to W) were used.

As the durum wheat (*Triticum durum*), dried seeds of one strain were used.

As the corn (*Zea mays*), dried seeds of one strain of dent corn were used.

As the soybean (*Glycine max*), dried seeds of Roundup Ready Soy-line progeny strain, which is a genetically modified soybean, were used.

As the rice (*Oryza sativa*), dried seeds of Koshihikari (Japonica variety) line were used.

As the barley (*Hordeum vulgare*), dried seeds of conventional five strains were used.

As the oats (*Avena sativa*), dried seeds of a commercially available strain were used.

As the rye (*Secale cereale*), dried seeds of two commercially available strains were used.

As the rapeseed (*Brassica napus*), dried seeds of canola species were used.

As the foxtail millet (*Setaria italica Beauvois*), dried seeds of glutinous husked foxtail millet species were used.

As the millet (*Panicum miliaceum Panicum*), dried seeds of glutinous husked millet species were used.

As the milo (*Sorghum subglabrescens*), dried seeds of a commercially available milo were used.

As the buckwheat (*Fagopyrum esculentum*), dried seeds of a conventional strain were used.

(2) Reagents

DNA extraction from samples was performed using the following reagents:

Sodium, lauryl sulfate (SDS) (special grade chemical) (Sigma Chemical Co.),

QIAGEN DNeasy Plant Maxi Kit. (QIAGEN GmbH), and

QIAGEN DNeasy Plant Mini Kit (QIAGEN GmbH).

Electrophoresis of DNA was performed using the following reagents:

Acetic acid (special grade chemical) (Wako Pure Chemical Industries, Ltd.),

Tris(hydroxymethyl)aminomethane (Tris) (special grade chemical) (Sigma Chemical Co.), Ethylenediaminetetraacetic acid (EDTA) (special grade chemical) (Sigma Chemical Co.), Agarose powder, LO3 "TaKaRa" (Takara Shuzo Co., Ltd.), Ethidium bromide (Sigma Chemical. Co.), Bromphenol blue (Sigma Chemical Co.), Xylene cyanol (Sigma Chemical Co.), DNA marker "1 kb Ladder" (New England Biolabs Inc.), and DNA marker "100 bp Ladder" (New England Biolabs Inc.).

Qualitative PCR was performed using the following reagents:

DNA polymerase, AmpliTaq Gold (Applied Biosystems, Inc.), and

×10 PCR buffer II (Applied Biosystems, Inc.).

Preparation and purification of plasmids were performed using the following reagents:

DNA polymerase, AmpliTaq Gold (Applied Biosystems, Inc.),

×10 PCR buffer II (Applied Biosystems, Inc.),

DNA polymerase, KOD (Toyobo Co., Ltd.),

×10 PCR buffer II (Toyobo Co., Ltd.),

TOPO TA Cloning Kit with TOP10F' Cells (Invitrogen Corp.),

Yeast extract (Difco Laboratories Inc.),

Tryptone peptone (Difco Laboratories Inc.),

NaCl (special grade chemical) (Wake Pure Chemical Industries, Ltd.),

Agar powder (Takara Bio Inc.),

D[−]-α-Aminobenzylpenicillin (Ampicilin) Sodium Salt (Sigma Chemical Co.),

QIAGEN Plasmid Maxi Kit (QIAGEN GmbH),

Ethanol (special grade chemical) (Wako Pure Chemical Industries, Ltd.),

2-Propanol (special grade chemical) (Wako Pure Chemical Industries, Ltd.),

Tris(hydroxymethyl)aminomethane(Tris) (special grade chemical) (Sigma Chemical Co.), Ethylenediaminetetraacetic acid (EDTA) (special grade chemical) (Sigma Chemical Co.), Restriction enzyme, EcoRI (Takara Shuzo Co., Ltd.), Restriction enzyme, SacI (New England Biolabs Inc.), Restriction enzyme, XbaI (New England Biolabs Inc.), Calf Intestinal Alkaline Phosphatase (Invitrogen Corp.), Phenol (special grade chemical) (Wako Pure Chemical Industries, Ltd.), Chloroform (special grade chemical) (Wako Pure Chemical Industries, Ltd.), and Isoamyl alcohol (special grade chemical) (Wako Pure Chemical Industries, Ltd.).

Quantitative PCR was performed using TaqMan Universal PCR Master Mix (Applied Biosystems, Inc.).

(3) Apparatuses

DNA extraction from samples was performed using a pulverizer, Multi Beads Shocker MB301 (Yasui Kikai Co., Ltd.).

DNA electrophoresis was performed using an electrophoresis apparatus, Mupid 2 (Advance Co., Ltd.).

Qualitative PCR was performed using a thermal cycler, PTC-200 (MJ Research Inc.).

Quantitative PCR was performed using a quantitative PCR apparatus, ABI PRISM 7700 Sequence Detector System (Applied Biosystems, Inc.).

(4) Conditions

Synthesis of primers and probes were contracted to Operon Technologies Inc.

Restriction enzyme digestion was performed in accordance with the manual of each restriction enzyme. That is, a restriction enzyme, a DNA solution, ×10 buffer solution attached to the enzyme, and distilled water were mixed and were subjected to a reaction, in general, at 37° C. for 2 hours.

DNA fragments after restriction enzyme digestion were separated by agarose gel electrophoresis. Purification from the gel was performed using a kit manufactured by QIAGEN GmbH. That is, a gel containing a target DNA was melted by heating, and the DNA was linked to a silica membrane. Subsequently, the silica membrane was washed with a solution containing ethanol, followed by elation with distilled water.

In dephosphorylation of the restriction enzyme-digested plasmid, the restriction enzyme-digested plasmid was desalted and then mixed with CIAP (manufactured by GIBCO Inc.) and an exclusive buffer, followed by reaction at 37° C. for 30 minutes. After the reaction, CIAP was inactivated by phenol treatment, and dephosphorylated plasmid was collected by ethanol precipitation.

Ligation of DNA was performed using a DNA Ligation kit ver. 2 manufactured by Takara Shuzo Co., Ltd. That is, a reaction mixture (soln I) of the kit was added to an equal amount of a mixture containing a target DNA, followed by leaving to stand at 16° C. for 30 minutes for DNA ligation.

Transformation was performed using Competent Cell *E. coli* DH5a manufactured by Toyobo Co., Ltd. On ice, 10 to 50 µL of competent cells was mixed with DNA and the mixture was left to stand for 30 minutes. After heat shock at 42° C. for 50 seconds, the mixture was placed on ice again for 2 minutes and was then added to 450 µL of a SOC medium warmed at 37° C., followed by incubation at 37° C. for 1 hour. This solution was applied to a Circle Grow medium$^{Amp+}$ plate at an amount of 100 µL/plate, followed by culturing at 37° C. for 16 hours.

Culturing for plasmid purification was performed using a medium, Circle Crow. Amp resistance was used as a selection pressure for plasmid production by using ampicillin at a final concentration of 100 µg/mL. The culturing was performed with a test tube shaker at 37° C. for 14 to 16 hours.

PCR was performed using AmpliTaq Gold polymerase manufactured by Applied Biosystems. Inc. at a reaction composition shown in Table 1 under reaction conditions shown in Table 2.

TABLE 1

| | |
|---|---|
| 10 × Buffer | 2.5 |
| 25 mM MgCl$_2$ | 1.5 |
| 2.5 mM dNTP | 2.0 |
| Primer pair | 2.5 |
| 5 µ/µl Taq | 0.25 |

TABLE 1-continued

| | |
|---|---|
| MQ H$_2$O | 15.75 |
| 50 ng/µl DNA | 0.5 |
| Total amount | 25.0 |

TABLE 2

| Step | Temperature ° C. | Time | Cycle No. |
|---|---|---|---|
| 1 | 95 | 10 min | |
| 2 | 95 | 30 sec | |
| 3 | 60 | 30 sec | 40 |
| 4 | 72 | 2 min | |
| 5 | 72 | 7 min | |
| 6 | 10 | Continuance | |

TA cloning was performed using a TOPO TA cloning system manufactured by Invitrogen Corp. The method was performed in accordance with the manual of the company.

DNA sequencing was performed using CEQ 8000 manufactured by Beckman Coulter Inc. The method was performed in accordance with the manual of the company. DTCS Quick Start master mix of the company was used as a kit.

Real time PCR was performed by a TaqMan method. TAKARA Premix Ex Taq (registered trade mark) (Perfect Real Time) Code No. RR039A was used as a kit. The real time PCR was performed using genomic DNAs as templates without diluting them. A master mix was prepared by mixing a premix, POX, a primer, and a probe as shown in Table 3. Subsequently, 16 µL/well of the master mix and 4 µL/well of a template DNA were mixed with each other, and a reaction was started under conditions shown in Table 4.

TABLE 3

| | Concentration | |
|---|---|---|
| Premix | 2 × | 10 |
| ROX | 50 × | 0.4 |
| Probe | 10 µM | 0.8 |
| Primer Pair | 5 µM each | 0.8 |
| H$_2$O | | 4.0 |
| Total amount | | 16.0 |

TABLE 4

| Step | Temperature | Time | Cycle | Ramp time |
|---|---|---|---|---|
| 1 | 50° C. | 2 min | 1 | Auto |
| 2 | 95° C. | 10 min | 1 | Auto |
| 3 | 95° C. | 5 sec | 40 | Auto |
| | 60° C. | 30 sec | | Auto |
| 7 | 20° C. | 1 min | 1 | Auto |

The template DNA (Plasmid pWIG04) was dilated as shown in Table 5 with a solution of 5 ng/µL of ColE1.

TABLE 5

| | Stock solution concentration $10^7$ copy/μl | Secondary stock solution concentration $10^5$ copy/μl | Well 2 | 3 | 4 | 5 | 6 | 7 | 8 |
|---|---|---|---|---|---|---|---|---|---|
| Stock solution volume μl | → | 4 | → 20 | 20 | | 20 | | 20 | |
| Diluted solution volume μl | | 396 | 180 | 180 | | 180 | | 180 | |
| Stock solution volume μl | | | 63.2 | → 20 | | 20 | | 20 | | 20 |
| Diluted solution volume μl | | | 136.8 | 180 | | 180 | | 180 | | 180 |
| Final concentration copy/μl | | $10^5$ | $3.16 \times 10^4$ | $10^4$ | $3.16 \times 10^3$ | $10^3$ | $3.16 \times 10^2$ | $10^2$ | $3.16 \times 10^1$ |

In the case of pulverizing a small amount of seeds, a multi-beads shocker was used. In pulverization, one seed and a metal cone were put in a 2-mL tube, and the tube was closed with a lid, followed by pulverization at 2000 rpm for 10 seconds twice. DNA was extracted directly from the powder of the pulverized seed.

Genomic DNAs were prepared using a QIAGEN Plant Mini Kit in accordance with the manual of the kit. Specifically, 400 μL of an AP1 solution and 4 μL of RNase A were added to the pulverized seed, followed by stirring. Subsequently, incubation at 65° C. for 10 minutes was performed with stirring two or three times during the incubation. Subsequently, 130 μL of AP2 was added thereto, followed stirring. The mixture was left to stand on ice for 10 minutes. After centrifugation (15000 rpm=20000 g, 5 min, room temperature), the whole quantity of the supernatant was applied to QIAshredder, followed by further centrifugation (15000 rpm, 2 min, room temperature). Subsequently, the pass-through supernatant was transferred to a separate container by decantation, 1.5 volumes (675 μL) of AP3/E was added thereto, and the mixture was stirred. A half of the volume was applied to a spin column, and centrifugation (10000 rpm, 1 min, room temperature) was performed. The flow-through was discarded, and the residue was applied to the same treatment as above. Subsequently, the column was placed in another tube, 500 μL of AW was added thereto, and centrifugation (10000 rpm, 1 min, room temperature) was performed. After retreatment, the flow-through was discarded, and the residue was further subjected to centrifugation (15000 rpm, 2 min, room temperature). The column was placed in another 1.5-mL tube, and 50 μL of AE was added thereto. The mixture was left to stand at room temperature for 5 minutes and was subjected to centrifugation (10000 rpm, 1 min, room temperature).

The DNA quantity was measured with a spectrophotometer (GeneSpec). In the quantification, a 5-mm cell was used at a dilution rate of 1. The eluate solution (AE) of the kit was used as a control.

Example 1

Construction of Standard Plasmid

Genomic DNA was extracted from a seed of domestic wheat strain A, and PCR was performed using the extracted DNA as a template and using primers shown in Table 6.

TABLE 6

| SEQ ID NO. | Sequence name | Sequence | Chain length |
|---|---|---|---|
| 2 | PRP3F | 5'-AAGCCACCGATGACTGACAAT-3' | 21 bp |
| 3 | PRPds3R | 5'-GGACAAAATGTGTCTTTCATGC-3' | 22 bp |

The resulting amplified DNA was TA cloned into a pCR4 TOPO vector using a TOPO TA cloning kit manufactured by Invitrogen Corp. Subsequently, the resulting plasmid was digested with restriction enzyme EcoRI, and a fragment of 350 bp was purified by cutting out the band from an electrophoresis gel. The pWIG02, which is described in International Publication No. WO2007/132760, was digested with restriction enzyme EcoRI and was then dephosphorylated. The purified fragment was ligated thereto to construct standard plasmid pWIG04. The inserted fragment was confirmed by restriction enzyme mapping of the resulting clone, and the whole sequence was then confirmed by DNA sequencing to be concordant with the target sequence.

Example 2

Search for Amplification Region in PRP Gene

A region of which detection amount is constant regardless of wheat strains was searched for the PRP gene. The wheat PRP gene has a homology with the PRP gene of barley. A region that does not cross over barley is therefore desirable as a primer. Accordingly, a primer region that does not cross over five barley strains and is amplified in three wheat stains was searched. The search was performed using a forward primer PRP8F in combination with a reverse primer PRPds6R or PRPds7P shown in Table 7. As shown in FIG. 1, the results show that in the combination of the forward primer PRP8P and the reverse primer PRPds6R, a PCR product is amplified from wheat, but a PCR product is not amplified from barley. In addition, it was also confirmed that in the combination of the forward primer PRP8F and the reverse primer PRPds7R, a PCR product is amplified from wheat, but is not amplified from barley.

TABLE 7

| SEQ ID NO. | Sequence name | Sequence | Chain length |
|---|---|---|---|
| 4 | PRP8F | 5'-GCACCCATGATGAGTACTACTATTCTGTA-3' | 29 bp |

TABLE 7-continued

| SEQ ID NO. | Sequence name | Sequence | Chain length |
|---|---|---|---|
| 5 | PRPds6R | 5'-TGCAAACGAATAAAAGCATGTG-3' | 22 bp |
| 6 | PRPds7R | 5'-TGTGTCTTTCATGCAAACGAAT-3' | 22 bp |

Example 3

Search of Probe

The investigation in Example 2 revealed that the region amplified by PRP8F and PRPds6R and the region amplified by PRP3F and PRPds7R are preferred as the PCR amplification regions of a species-specific gene. Accordingly, a probe suitable for the primers was designed for these regions. The probe was designed using primer design support software, Primer Express or Primer3 (The development of Primer3 and the Primer3 web site was funded by Howard Hughes Medical institute and by the National Institutes of Health, National Human Genome Research Institute. under grants R01-HG00257 (to David C. Page) and P50-HG00098 (to Eric S. Lander): http://frodo.wi.mit.edu/cgi-bin/primer3/primer3_www.cgi). Table 8 shows the sequence of the designed probe. A fluorescence-labeled probe was synthesized from the designed probe sequence. In the fluorescence-labeled probe, the 5'-end was modified with FAM as the fluorescent material, and the 3'-end was modified with TAMRA as a quencher.

TABLE 8

| SEQ ID NO | Sequence name | Sequence | Chain lenght |
|---|---|---|---|
| 7 | PRP-Taq3 | 5'-GGTATATGTTCATCTGTGCACATGACTC-3' | 28 bp |

Example 4

Establishment of Conditions for Real Time PCR

Conditions for real time PCR by a TaqMan method using the fluorescence-labeled probe synthesized in Example 3 and using standard plasmid pWIG04 as a template were established. Specifically, optimal conditions for real time PCR were found by changing each parameter of the primer concentration, the probe concentration, the PCR reaction temperature, and the time. The selected conditions are shown below.

TABLE 9

| | Concentration | |
|---|---|---|
| Premix | 2 × | 10 |
| ROX | 50 × | 0.4 |
| Probe | 10 μM | 0.8 |
| Primer Pair | 5 μM each | 0.8 |
| H$_2$O | | 4.0 |
| Total amount | | 16.0 |

TABLE 10

| Step | Temperature | Time | Cycle | Ramp time |
|---|---|---|---|---|
| 1 | 50° C. | 2 mins | 1 | Auto |
| 2 | 95° C. | 10 min | 1 | Auto |
| 3 | 95° C. | 5 sec | 40 | Auto |
| | 60° C. | 30 sec | | Auto |
| 4 | 20° C. | 1 min | 1 | Auto |

Example 5

Confirmation of University of Wheat Strains

Figure 2:
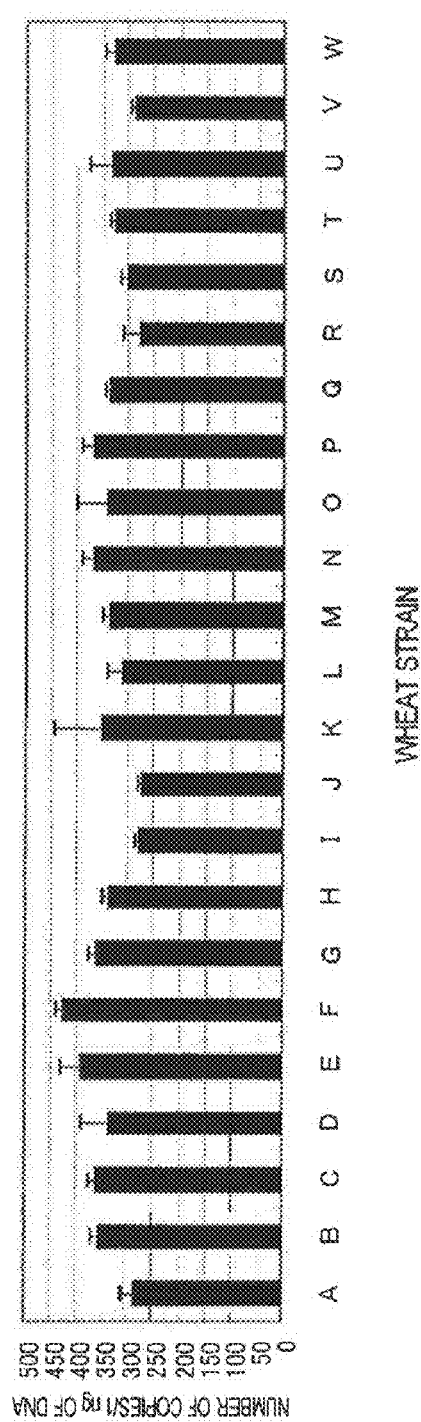
FIG. 2 is a graph showing the detection amounts of wheat species-specific DNA according to Example 5 of the present invention.

After determination of optimal conditions for real time PCR in Example 4, detection amounts of a wheat species-specific DNA measured by real time PCR by the TaqMan method were compared for 23 wheat strains. As the primers, PRP8F identified as SEQ ID NO: 4 and PRPds6R identified as SEQ ID NO: 5 were used. As the probe, PRP3-Taq identified as SEQ ID NO: 7 was used. As shown in FIG. 2, the results show that PRP is detected in all 23 wheat strains and that PRP has university as a wheat species-specific gene.

Example 6

Validation of Specificity

Figure 3:
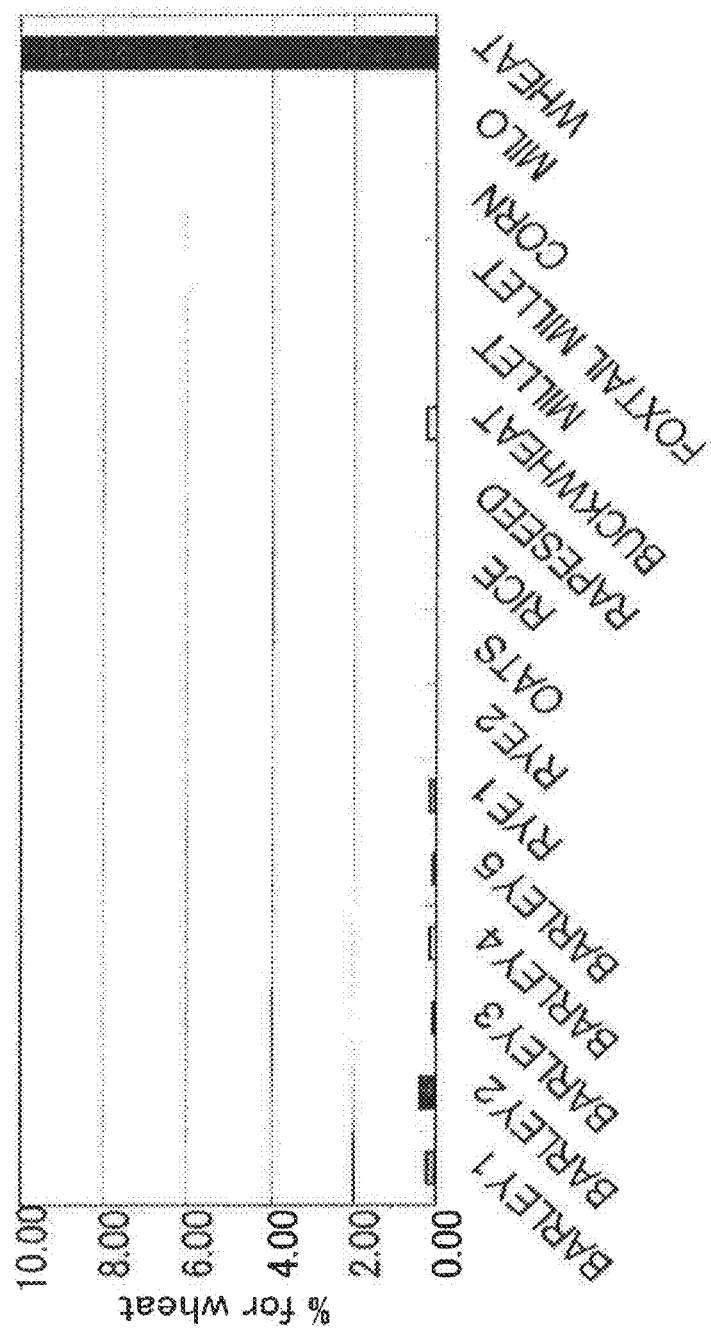
FIG. 3 is a graph showing the results of a specificity test according to Example 6 of the present invention.

In order to confirm that the method according to the embodiment of the present invention does not cross over crops other than wheat, a specificity test was performed. The other crops used were barley, oats, rye, rice, milo, rapeseed, corn, buckwheat, foxtail millet, and millet. DNAs were extracted from these crops, and real time PCR was performed using the extracted DNAs as templates under the optimal conditions determined in Example 4. As the primers, PRP8F identified as SEQ ID NO: 4 and PRPds6R identified as SEQ ID NO: 5 were used. As the probe, PRP-Taq3 identified as SEQ ID NO: 7 was used. As shown in FIG. 3, the non-specific detection rates of these crops with respect to the value detected in wheat were 0.2% or less in all five barley strains and 0.05% or less in other crops. Thus, the non-specific detection rates were vastly lower than the standard error in wheat detection, which shows that these crops other than wheat do not affect the quantification of the wheat species-specific gene.

Example 7

Investigation of Errors Among Different Types of Quantitative PCR Apparatuses

Figure 4:
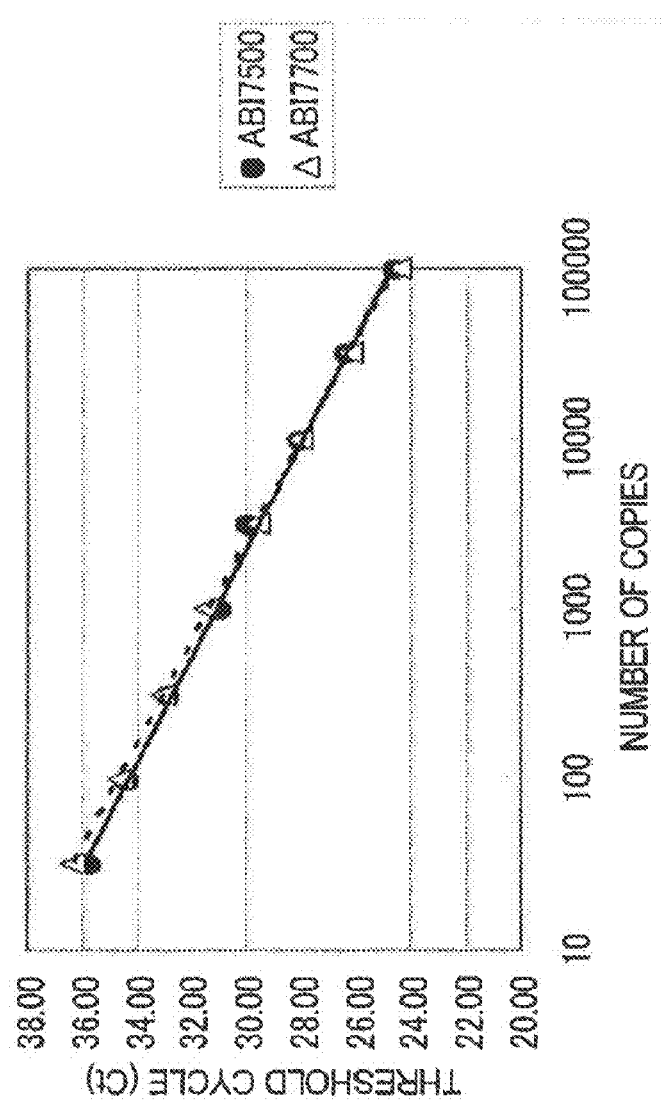
FIG. 4 is a graph showing the results of investigation of errors caused by difference in model of the quantitative PCR apparatuses according to Example 7 of the present invention.

Many types of quantitative PCR apparatuses are commercially available and may differ in performance. Accordingly, it was investigated using the primer set and probe according to the embodiment of the present invention whether errors in quantitative value are caused by difference in type of quantitative PCR apparatuses. As the quantitative PCR apparatuses, PRISM 7700 and Applied Biosystems 7500 real time PCR system manufactured by Applied Biosystems, Inc. were used. As the PCR reaction reagent, TAKARA Premix Ex Taq (registered trade mark) (Perfect Real Time) Code No. RR039A was used. PRP8F and PRPds6R were used as a primer set, and PRP-Taq3 was used as a probe. As a template, plasmid pWIG04 described in Example 1 was used. A dilution series of plasmid pWIG04 was prepared so as to contain 10000, 31623, 10000, 3162, 1000, 316, 100, or 32 copies per reaction. The quantitative PCR reaction was performed as in Example 4. As shown in FIG. 4, the results show that both apparatuses perform amplification in a similar manner to each other in the dilution range of the template DNA. It was thus confirmed that the primer set and the probe according to the embodiment of the present invention do not cause errors due to difference in type of apparatuses.

DESCRIPTION OF SEQUENCE LISTING

SEQ ID NOs: 1 to 17 described in the sequence listing of the specification are as follows:

SEQ ID NO: 1 is a partial nucleotide sequence of a PRP gene.

SEQ ID NO: 2 is the nucleotide sequence of forward primer PRP3F.

SEQ ID NO: 3 is the nucleotide sequence of reverse primer PRPds3R.

SEQ ID NO: 4 is the nucleotide sequence of forward primer PRP8F.

SEQ ID NO: 5 is the nucleotide sequence of reverse primer PRPds6R.

SEQ ID NO: 6 is the nucleotide sequence of reverse primer PRPPds7R.

SEQ ID NO: 7 is the nucleotide sequence of a probe.

Throughout the specification, when nucleotides are denoted by symbols, symbols by the IUPAC-IUB Commission on Biochemical Nomenclature or common symbols used in the art are used. Examples of the symbols are shown below.

a: adenine, t: thymine, g: guanine, c: cytosine.

Note that the GenBank number of PRP is X52472; the GenBank number of PRP-EST is CV772819; the GenBank number of barley PRP is BE601897; and the GenBank number of barley PRPcDNA is CB881611.

The invention claimed is:

1. A circular DNA comprising a non-natural vector inserted with a nucleotide sequence capable of being amplified by polymerase chain reaction using a primer pair comprising a first primer and a second primer, wherein:
   (i) the first primer comprises the nucleotide sequence of SEQ ID NO: 4, and the second primer comprises the nucleotide sequence of SEQ ID NO: 5; or
   (ii) the first primer comprises the nucleotide sequence of SEQ ID NO: 4, and the second primer comprises the nucleotide sequence of SEQ ID NO: 6, the circular DNA further comprises at least one DNA consisting of a sequence specific to a strain of genetically modified wheat, and the sequence specific to a strain of genetically modified wheat comprises an exogenous DNA sequence inserted in the genome of the genetically modified wheat.

* * * * *

```
                            SEQUENCE LISTING

<160> NUMBER OF SEQ ID NOS: 7

<210> SEQ ID NO 1
    <211> LENGTH: 325
    <212> TYPE: DNA
    <213> ORGANISM: Triticum aestivum

<400> SEQUENCE: 1
aagccaccga tgactgacaa ttgatgtgat actcacatat gacagctgaa ggaggagatc        60 gacccgtcc ggagccacga tgtgctattt ctagaataag tggcatagta tccggttagc       120
gagatagtga tgatgcatct ttttgtattc cttgtattcc accattcctt ttagtttctg       180
ttgttccatg cacccatgat gagtactact attctgtaat tatcatttgc gtgttggtat       240
atgttcatct gtgcacatga ctcagttgtt ctttcgtgta gatacacatg cttttattcg       300
tttgcatgaa agacacattt tgtcc                                             325

<210> SEQ ID NO 2
    <211> LENGTH: 21
    <212> TYPE: DNA
    <213> ORGANISM: artificial
    <220> FEATURE:
    <223> OTHER INFORMATION: PCR primer PRP3F

<400> SEQUENCE: 2
aagccaccga tgactgacaa t                                                  21

<210> SEQ ID NO 3
    <211> LENGTH: 22
    <212> TYPE: DNA
    <213> ORGANISM: artificial
    <220> FEATURE:
    <223> OTHER INFORMATION: PCR primer PRPds3R

<400> SEQUENCE: 3
ggacaaaatg tgtctttcat gc                                                 22

<210> SEQ ID NO 4
    <211> LENGTH: 29
    <212> TYPE: DNA
    <213> ORGANISM: artificial
    <220> FEATURE:
    <223> OTHER INFORMATION: PCR primer PRP8F

<400> SEQUENCE: 4
```

| | |
|---|---|
| gcacccatga tgagtactac tattctgta | 29 |

<210> SEQ ID NO 5
<211> LENGTH: 22
<212> TYPE: DNA
<213> ORGANISM: artificial
<220> FEATURE:
<223> OTHER INFORMATION: PRPds6R

<400> SEQUENCE: 5

| | |
|---|---|
| tgcaaacgaa taaaagcatg tg | 22 |

<210> SEQ ID NO 6
<211> LENGTH: 22
<212> TYPE: DNA
<213> ORGANISM: artificial
<220> FEATURE:
<223> OTHER INFORMATION: PPRPds7R

<400> SEQUENCE: 6

| | |
|---|---|
| tgtgtctttc atgcaaacga at | 22 |

<210> SEQ ID NO 7
<211> LENGTH: 28
<212> TYPE: DNA
<213> ORGANISM: artificial
<220> FEATURE:
<223> OTHER INFORMATION: PRP-Taq3

<400> SEQUENCE: 7

| | |
|---|---|
| ggtatatgtt catctgtgca catgactc | 28 |